(12) United States Patent
Piergallini et al.

(10) Patent No.: US 8,075,875 B2
(45) Date of Patent: Dec. 13, 2011

(54) TEETH WHITENING COMPOSITION AND METHODS

(75) Inventors: Remigio Piergallini, Grottammare (IT); Nicolas Loupis, Athens (GR)

(73) Assignee: KLOX Technologies Inc., Montreal (CA)

( * ) Notice: Subject to any disclaimer, the term of this patent is extended or adjusted under 35 U.S.C. 154(b) by 0 days.

(21) Appl. No.: 11/598,206

(22) Filed: Nov. 9, 2006

(65) Prior Publication Data

US 2007/0128132 A1    Jun. 7, 2007

Related U.S. Application Data

(60) Provisional application No. 60/735,072, filed on Nov. 9, 2005.

(51) Int. Cl.
*A61K 8/19* (2006.01)
(52) U.S. Cl. .................................. 424/53; 433/25
(58) Field of Classification Search ............... 424/53
See application file for complete search history.

(56) References Cited

U.S. PATENT DOCUMENTS

| | | | |
|---|---|---|---|
| 3,595,798 A | 7/1971 | Smith et al. | |
| 3,728,446 A * | 4/1973 | Roberts et al. | 424/49 |
| 4,891,211 A * | 1/1990 | Winston | 424/52 |
| 5,785,527 A * | 7/1998 | Jensen et al. | 433/215 |
| 5,858,332 A * | 1/1999 | Jensen et al. | 424/53 |
| 6,030,222 A | 2/2000 | Tarver | |
| 6,036,493 A | 3/2000 | Sharma | |
| 6,149,895 A | 11/2000 | Kutsch | |
| 6,162,055 A | 12/2000 | Montgomery et al. | |
| 6,254,388 B1 | 7/2001 | Yarborough | |
| 6,343,933 B1 | 2/2002 | Montgomery et al. | |
| 6,361,329 B1 | 3/2002 | Dekker et al. | |
| 6,365,134 B1 | 4/2002 | Orlowski et al. | |
| 6,387,353 B1 | 5/2002 | Jensen et al. | |
| 6,391,283 B1 | 5/2002 | Jensen et al. | |
| 6,440,396 B1 | 8/2002 | McLaughlin | |
| 6,485,709 B2 | 11/2002 | Banerjee et al. | |
| 6,488,914 B2 | 12/2002 | Montgomery | |
| 6,514,543 B2 | 2/2003 | Montgomery | |
| 6,536,628 B2 | 3/2003 | Montgomery | |
| 6,846,182 B1 | 1/2005 | Sibner | |
| 6,905,672 B2 * | 6/2005 | Rajaiah et al. | 424/49 |
| 2004/0136971 A1 * | 7/2004 | Scharp et al. | 424/93.7 |
| 2005/0026298 A1 | 2/2005 | Bickett et al. | |

FOREIGN PATENT DOCUMENTS

| | | |
|---|---|---|
| WO | WO-97/21420 A1 | 6/1997 |
| WO | WO-98/23219 A1 | 6/1998 |
| WO | WO-98/30169 A1 | 7/1998 |
| WO | WO-99/40870 A1 | 8/1999 |
| WO | WO-02/22097 A1 | 3/2002 |
| WO | WO-2004/028498 A1 | 4/2004 |

OTHER PUBLICATIONS

FDA, Product Classification Database Search, Device: Eosin y: database updated Jun. 6, 2008.*
FDA, Color Additive Status List: http://www.cfsan.fda.gov/~dms/opa-appc.html.*
Sun, Grace, "Lasers and Light Amplification in Dentistry," retrieved online at http://www.sundds.com/laser/ on Jun. 23, 2005.
"Resources: Fluorochrome Absorption Emission Wavelenghts" [Online] XP002449595 Retrieved from the Internet: URL: http://www.sciencegateway.org/ressources/fael.html>[retrieved on Sep. 6, 2007] see p. 2: Rhodamine WT emission nm 555 p. 2.

* cited by examiner

*Primary Examiner* — Frederick Krass
*Assistant Examiner* — Walter Webb
(74) *Attorney, Agent, or Firm* — Ropes & Gray LLP

(57) ABSTRACT

Disclosed herein are teeth whitening compositions generally including an oxidizing agent (e.g., a peroxide), and an activating agent that has an emission wavelength between about 400 nm and about 570 nm (e.g., Eosin B). Methods of employing these compositions to whiten teeth, methods of making these compositions and kits that include some or part of the composition ingredients, are also described.

9 Claims, No Drawings

TEETH WHITENING COMPOSITION AND METHODS

FIELD OF THE INVENTION

The present invention relates generally to teeth whitening compositions. More specifically, the invention relates to teeth whitening compositions and kits that can be employed to provide a desired whitening effect (e.g., at least two shades of whitening) in less than 20 minutes (e.g., in about 1 minute) without significant post-treatment sensitivity.

BACKGROUND OF THE INVENTION

Peroxide and peroxyacid compounds, such as hydrogen peroxide and carbamide peroxide, have been disclosed as useful in teeth whitening compositions. Application of UV or visible light from, e.g., Argon lasers, has been employed to accelerate whitening after application of peroxide compositions to the teeth. Additionally, whitening compositions have been described that include compounds capable of absorbing light and converting it to heat or chemical energy, such as the metal-ligand complexes and metal chelate precursors described in U.S. Pat. No. 6,343,933 to Montgomery et al.

Red dyes have also been employed to absorb visible or UV energy and produce heat in a bleaching composition as described, e.g., in U.S. Pat. No. 6,485,709 to Banerjee et al. This patent also describes attempts to further enhance such compositions by adding metal ions, an organo-metallic enzyme (e.g. catalase), or using high pH (e.g., above 7) to destabilize or activate the decomposition of hydrogen peroxide. Teeth whitening compositions have also been described that include violet or blue-violet dyes to counter-stain yellow teeth in U.S. Pat. No. 6,030,222 to Tarver. Rhodamine B dye has been employed in a teeth whitening composition as described in WO 02/22097 to Verheyen et al.

Tooth sensitivity following treatment, and the time required for teeth whitening compositions (typically requiring about an hour of time or multiple applications or both), however, remains a significant drawback.

SUMMARY OF THE INVENTION

The present invention provides novel compositions and methods that whiten teeth in a surprisingly short amount of time (e.g., about 1 to 10 minutes) and with minimal or no sensitivity post-treatment. The invention is based, in part, on the discovery that the use of the dyes described herein dramatically accelerates the whitening process.

Without wishing to be bound to any particular theory, it is believed that inclusion of these dyes significantly enhances the compositions of the invention at least because it is believed that dentin transmits green light and absorbs blue light. Accordingly, the dyes of the present invention enhance whitening not only at the surface of the tooth, but also may be transmitting light into the tooth to enhance the alteration of color agents by radicals that have penetrated into the tooth surface.

Another advantage of the present invention is that the compositions can be effective when applied only for a short period of time (e.g., 1 minute in some embodiments). Accordingly, sensitivity due to, e.g., percolation of hydrogen peroxide to the pulp tissue causing (e.g., pulpal inflammation), may be minimized or eliminated. Another advantage of the present invention is that the compositions do not require compounds that generate heat, and therefore, discomfort associated with compositions that generate heat may be minimized or eliminated. Yet another advantage is that dyes can be used (e.g., Eosin B) that are less toxic than dyes such as Rhodamine B.

In one aspect, the present invention features a tooth whitening composition which includes an oxidizing agent and an activating agent having an emission wavelength between about 400 nm and about 570 nm.

In one embodiment, the activating agent is capable of emitting green light, blue light or blue-green light, and/or absorbs green light, blue light or blue-green light. In another embodiment, the activating agent comprises Eosin B, Erythrosin B, or both.

In another embodiment, the composition further includes a stabilizing agent. In one embodiment, the stabilizing agent is sodium acetate.

In one embodiment, the composition further includes a thickening agent. In one embodiment, the thickening agent is silicon dioxide and/or fumed silica having a particle size less than one micron.

In one embodiment, the composition further includes a hydrophilic gelling agent. In another embodiment, the composition further includes an accelerator agent. In some embodiments, the accelerator agent includes sodium perborate.

In one embodiment, the pH of the composition is between about 8 and about 10.

The invention also features a method for tooth whitening including applying the tooth whitening composition of the present invention to at least one tooth, and exposing the tooth whitening composition to actinic light such that the tooth is whitened at least about one shade. In one embodiment, the tooth is whitened at least about two shades in less than about 10 minutes or in less than about 5 minutes.

In one embodiment, post-treatment sensitivity is insignificant or eliminated.

In one embodiment, the tooth is exposed to the tooth whitening composition for less than 5 seconds per application.

The invention also features a kit for tooth whitening including a tooth whitening composition of the invention and an apparatus for preparing and/or applying the composition.

The invention also features a kit for tooth whitening including a tooth whitening composition of the invention and instructions for determining a composition application time to achieve a desired whitening effect.

The invention also features a method for tooth whitening including at least one application of actinic light and a tooth whitening composition to at least one tooth such that the tooth is whitened at least about two shades with less than about 1 minute of total exposure to actinic light. In one embodiment, the tooth is whitened at least about three shades in less than about 30 seconds. In another embodiment, there is no significant post-treatment sensitivity.

DETAILED DESCRIPTION OF THE PREFERRED EMBODIMENTS

In order to more clearly and concisely describe the subject matter of the claims, the following definitions are intended to provide guidance as to the meaning of specific terms used in the following written description, examples and appended claims.

The term "accelerating agent" refers to any agent capable of accelerating and/or contributing to the completion of radical generation (e.g., sodium perborate).

The term "actinic light" refers to light energy capable of being absorbed by an activating agent.

The term "activating agent" refers to any agent capable of absorbing actinic light. Preferably, the activating agent enhances and/or accelerates the dispersion of light energy, or otherwise enhances and/or activates the decomposition of an oxidizing agent. Activating agents include agents capable of absorbing light energy and emitting light energy, e.g., fluorochromes. Suitable activating agents include, e.g., Eosin B and Erythrosin B.

The term "oxidizing agent" refers to any agent capable of oxidizing, and also includes precursors of compounds capable of oxidizing. Examples of oxidizing agents include, but are not limited to, peroxide, peroxy acid, hydrogen peroxide, carbamide peroxide, alkali metal peroxides, alkali metal percarbonates, peroxyacetic acid, and alkali metal perborates.

The term "post-treatment sensitivity" refers to sensitivity or instant pain experienced by a subject after a tooth whitening procedure. Sensitivity can include, but is not limited to, stimuli such as temperature and pressure. Instant pain typically occurs without stimuli. The terms "significant sensitivity" or "significant post-treatment sensitivity" and the like, refer to significant discomfort post-treatment, including sensitivity and/or instant pain for more than four hours. The term "insignificant pain" refers to minimum sensitivity to stimuli such as temperature and/or pressure for less than four hours post-treatment.

The term "stabilizing agent" refers to any agent that stabilizes one or more agents of the composition (e.g., an oxidizing agent such as hydrogen peroxide). The stabilizing agent can act to stabilize the agent or agents against spontaneous or unwanted reactivity in use and/or in storage. Suitable stabilizing agents include sodium acetate. In some instances, the stabilizing agent can stabilize hydrogen peroxide for about one year.

The term "total exposure to actinic light" refers to the total time a tooth is exposed to actinic light including multiple applications of actinic light over the course of a treatment session.

The term "transparent" refers to a composition capable of at least 70% transmission of light. The term "translucent" refers to a composition capable of at least about 40% transmission of light. The light referred to can be, e.g., actinic light (e.g., from a laser), emitted light (e.g., from a fluorochrome), or both.

The term "translucency agent" refers to any agent capable of increasing the translucency of a composition. Such agents can increase translucency, e.g., upon addition to the composition, upon activation (e.g., by heat, actinic light and/or emitted light), or both.

When ranges are disclosed herein (e.g., wavelength, pH, concentration, particle sizes, and whitening ranges) all individual values and ranges within the disclosed ranges are regarded as part of and encompassed by the present invention. All concentrations are provided in weight % of the composition unless indicated otherwise.

Where "a", "an" or the like is used herein, these articles are used in the open or non-restrictive sense, e.g., to indicate "at least one" or "one or more." Similarly, the term "or" is used in the open or nonrestrictive sense, i.e., to mean "and/or." Accordingly, the terms "or" and "and/or" are used interchangeably and are meant to have the same meaning.

In one aspect, the present invention provides tooth whitening compositions that include an oxidizing agent (e.g., hydrogen peroxide), and an activating agent that has an emission wavelength between about 400 nm and about 570 nm (e.g., Eosin B or Erythrosin B or both). The composition can also include additional agents including, but not limited to, pH adjusting agents, thickening agents, stabilizing agents, accelerating agents, gelling agents, translucency agents.

The oxidizing agent can be any oxidizing agent known in the art. In one embodiment, the oxidizing agent includes hydrogen peroxide or sodium perborate or both. Additionally or alternatively, the oxidizing agent can include carbamide peroxide, alkali metal peroxides, alkali metal percarbonates, alkali metal perborates or combinations of these compounds. The oxidizing agents can be, e.g., liquid, gel, or paste compositions capable of interacting with the activating compound when exposed to actinic light.

The concentration of the oxidizing agent can be varied in the present invention. In one embodiment, the oxidizing composition includes a hydrogen peroxide, e.g., in a range of about 1% to about 70%. In a further embodiment, the oxidizing composition includes about 50% hydrogen peroxide.

The activating agent can include any agent with an emission wavelength between about 400 nm and about 570 nm. In another embodiment, the activating agent emits light in the range of between about 435 nm and about 520 nm. In one embodiment, the activating agent emits light in the range of between about 520 nm and about 565 nm. In certain embodiments, the agent both absorbs and emits light in the above ranges. In one embodiment, the activating agent emits green light. In another embodiment, the activating agent emits blue-green light. In one embodiment the activating agent both absorbs and emits green light.

In one embodiment, the activating agent includes Eosin B or Erythrosine B or both. In another embodiment, the whitening composition includes in the range of about 0.5% to about 0.8%, or between about 0.2% and about 1.2%, or less than about 12%, of Eosin B. In yet another embodiment, the composition includes about 0.2 to about 12% of Eosin B and from about 0.01% to about 0.1%, or about 0.005% and about 0.15%, of Erythrosine B. Without wishing to be bound to any particular theory it is believed that the combination of Eosin B and Erythrosine B has a synergistic effect. It is believed this synergistic effect may be related to the close absorption peaks of the dyes. It is further believed that because Eosin B and Erythrosine B re-emit green light, that this green light can and may be further absorbed (or re-absorbed) by the fluorochromes so that light energy is not dissipated as in conventional compositions. This absorbed and re-emitted light not only penetrates throughout the bleaching gel, but also is transmitted into the enamel and dentin. Dyes such as Eosin B are also advantageous as they are significantly less toxic than dyes such as Rhodamine B.

Without wishing to be bound to any particular theory, it is believed that because dentin and enamel transmit green light, light in this range can be transmitted into the dentin and/or enamel of the tooth, causing excitation of electrons in specific chemical bonds within the activating agent and tooth chromaphores, making them more susceptible to be attacked by free radicals. The activating agents of the invention can include blue-green and/or blue emitting dyes. Accordingly, the present invention is based, at least in part, on the discovery that the use of the activating agents of the invention significantly enhance and/or contribute to the enhancement of a whitening effect in a fraction of the time required by conventional compositions. Because the teeth are only exposed to the whitening composition for a fraction of the time as compared to conventional teeth whitening compositions, superficial cracks and crevices, caused by prolonged exposure to free radicals, can be reduced or eliminated. Because decalcification can occur in the cracks and crevices caused by prolonged exposure to free radicals, stains more easily return as the decalcified enamel acts as a sponge. In the present invention, the decreased exposure time to free radicals reduces the possibility of crevices and cracks, thus leading to a significantly prolonged or permanent whitening effect for deeper pigments. Moreover, prolonged periods of exposure cause the enamel to become brittle. It is believed that the composition and methods of the present invention avoid compromise of the enamel.

In one embodiment, the activating agent or agents not only are capable of emitting light in the wavelength range from about 400 nm to about 570 nm, but also absorb light in the wavelength range from about 400 nm to about 570 nm. Such an activating agent is activated by light in the wavelength range of from about 400 nm to about 570 nm. Accordingly, in one embodiment the activating agent absorbs light in the wavelength range of about 400 nm to about 570 nm. In another embodiment, the activating agent absorbs light at a wavelength between about 470 nm to about 550 nm. This embodiment therefore allows for the optimal absorption of energy from the actinic light and the optimal transmission through dentin and enamel.

Without wishing to be bound to any particular theory, it is also believed that activating agents of the present invention, when exposed to actinic light, can accelerate the dispersion of light energy which consequently leads to an instantaneous and complete photochemical activation of the peroxide within the gel. It is believed that the gel mass better transmits light in the wavelength range of about 400 nm to about 570 nm, so that when an activating agent is exposed to actinic light, the dispersion of the light energy leads to an accelerated photochemical activation of the peroxide. Together, these embodiments allow for optimal absorption by the activating agent of energy from the actinic light and the optimal transmission through the composition, dentin and enamel.

In one embodiment, the composition also includes a stabilizing agent. In one embodiment, the stabilizing agent stabilizes the peroxide concentration in the composition for days, weeks, months, a year or several years. In one embodiment, the stabilizing agent not only stabilizes the oxidizing agent, but also is a pH modifier and/or stabilizer. In another embodiment, the stabilizing agent is sodium acetate. In one embodiment, sodium acetate is added until the desired pH is attained. In yet another embodiment, the composition includes between about 0.1% and about 50% stabilizing agent. Any value or range within this range is meant to be encompassed.

In one embodiment, the stabilizing agent is selected from the group consisting of antioxidants such as sodium sulfite, metal chelators (e.g., EDTA), and stabilizers (e.g., tin salts, phosphoric acid, and tin sulphonates). In some embodiments, the stabilizing agent scavenges or otherwise isolates or removes from solution, metal ions that can potentially destabilize the hydrogen peroxide.

In one embodiment, the stabilizing agent is or includes sodium acetate (e.g., sodium acetate trihydrate). Sodium acetate has been found to inhibit spontaneous reactivity of hydrogen peroxide and therefore can provide improved stability.

In one embodiment, the pH of the composition is in or adjusted to the range of from about 4 to about 10. In alkaline conditions, with a pH from about 8 to about 10, the stronger free radical, perhydroxyl ions, can be generated. Perhydroxyl free radicals are capable of reacting not only with yellow and brown stains but even with grey chromophores situated deeper in the tooth structure. In further embodiments, the pH of the composition is between about 5 and about 7, or between about 5 and about 6. In certain embodiments the pH is about 6.

Suitable pH adjusting agents include, but are not limited to, sodium hydroxide, potassium hydroxide, ammonium hydroxide, sodium carbonate, potassium carbonate, TRIS, and triethanolamine, or any other salt of an alkaline base which is safely used in the mouth. In another embodiment, the pH adjusting agent is sodium perborate. In certain embodiments of the invention, a single component may act as a pH adjusting agent or as a stabilizing agent or may serve both functions. In one embodiment, sodium acetate acts as a pH adjusting agent and as a stabilizing agent. In further embodiments, the pH adjusting agent is of the group consisting of sodium bicarbonate, calcium bicarbonate, sodium carbonate and calcium carbonate.

Additionally or alternatively, the composition can include a thickening agent to improve the ease of application of the composition to the teeth such that even and effective coverage is more readily achieved. Suitable thickening agents include but are not limited to mixed silica-aluminum oxides, long chain hydrocarbons such as synthetic carbomers (e.g., Carbopol), triethanolamine (e.g., Trolamine), and water soluble poly(ethylene oxide) resins (e.g., Polyox). Suitable thickening agents also include amide starches.

It has been found that using an agent which has a particle size in the range from about 0.2 microns (μm) to about 0.7 μm provides for more widespread dispersion of the oxidizing agent on the particle surface. Accordingly, in one embodiment, the activating agent has a particle size below about 2 microns or below about 1 micron. In other embodiments, the agent has a particle size below about 0.8, 0.7, 0.6, 0.5, 0.4, 0.3, or 0.2 microns. In other embodiments, the activating agent has a particle size between about 0.1 and about 0.8, between about 0.2 and about 0.7, or between about 0.3 and about 0.6 microns.

Additionally or alternatively, the thickening agent can include fumed silica and/or any other inert inorganic material that may be used as a carrier and can aid in the delivery of active oxygen to the tooth surface. Fumed silica of a small particle size (e.g., between about 0.2 microns and about 0.4 microns), can provide efficient dispersion of hydrogen peroxide and reflection of light energy within the oxidizing composition.

In some embodiments, the compositions of the invention include a reaction accelerator or accelerating agent. In one embodiment, the composition includes sodium perborate. Sodium perborate has selective reactivity with hydrogen peroxide in forming free radicals (reacts with water to release hydrogen peroxide). The use of one or more activating agents (e.g., sodium perborate) can be advantageous because they can absorb and retain heat generated in the composition by, e.g., actinic light, thus restricting any such heat to the gel in order to accelerate the reaction without heating the tooth, which can cause sensitivity. In addition, acceleration of the reaction means that the composition can be removed more quickly than conventional compositions thereby decreasing exposure of the patient to the composition and resulting sensitivity and/or other damage to tissues and teeth.

In one embodiment, the compositions of the invention include between about 0.8% and about 15%, or between about 0.3% and about 18% accelerator agent.

In further embodiments, the compositions of the invention include a gelling agent. Preferably the gelling agent is also a translucency agent. For example, a hydrophilic gelling agent can be employed to increase the translucency of the resulting composition or gel.

In some embodiments, the nature of the gelling agent (e.g., its hydrophilic nature) prevents vaporization of the gel when exposed to actinic light, thus improving hydration of the coated tooth area. Increased hydration of the teeth and surrounding tissues is associated with decreased discomfort and sensitivity. In one embodiment, the gelling agent can include, for example, one or more modified starches and/or glucose. In one embodiment, modified starches and/or glucose are activated in cold water. In some embodiments, the gelling agent further enhances the consistency of the composition, facilitating the application to the tooth surface.

The translucency agent can enhance translucency or transparency upon addition to the composition and/or upon activation by, e.g., actinic light, emitted light and/or heat. In one embodiment, it minimizes vaporization of the composition. Additionally or alternatively, the gelling and/or translucency agent minimizes any thermal effects by absorbing any heat generated in the composition.

In one embodiment the composition is a translucent composition. In another embodiment the composition is a transparent composition. In certain embodiments, the composition is translucent or transparent to the actinic light it will be exposed to (e.g., green, blue-green or blue light).

In one embodiment, the composition includes an oxidizing agent (e.g., hydrogen peroxide), an accelerating agent (e.g., sodium perborate), an activating agent (Eosin B or Erythrosin B or both), a stabilizing agent (e.g., sodium acetate trihydrate), a pH adjusting agent, a thickening agent (e.g., fumed silica or silicon dioxide or both), and a gelling agent. In one embodiment, the pH of the composition is from about 6 to about 10. In some embodiments, the pH of the composition is from about 8 to about 10.

Another aspect of the invention provides a method for tooth whitening including applying a tooth whitening composition of the present invention to at least one tooth, and exposing the tooth whitening composition to actinic light to activate the oxidizing agent. The composition may be any of the compositions described herein.

In one embodiment, the method for bleaching the teeth is performed in a dentist's office or dental operatory under ordinary conditions. The composition can be mixed chair-side and applied to the surfaces of as many teeth as are desired to be whitened. Alternatively, the composition can be provided without the need for mixing chair-side. Thereafter, the composition can be exposed to actinic light to accelerate decomposition of the oxidizing agent and the formation of free radicals. In one embodiment, premixes can be prepared with some or all of the ingredients and then mixed chairside and applied to the teeth. In one embodiment, a hydrogen peroxide/sodium acetate solution premix can be prepared and stored prior to use. Additionally or alternatively, some or all of the remaining ingredients can also be separately premixed and stored prior to use. Such premixes can be stored, e.g., for at least about one year.

The compositions of the invention can be used to whiten teeth discolored by any agent or disorder. For example, the compositions may be used to whiten discoloration due to stains (e.g., tobacco, coffee, tea and/or food stains), fluorosis, developmental disturbances, bacteria, genetics, tetracycline antibiotics, trauma, blood decomposition, pigments present during development of teeth, etc.

Any source of actinic light can be used and preferably it is capable of emitting light in a wavelength appropriate to the activating agent employed in the composition. In one embodiment, e.g., an argon laser is used. In another embodiment, a potassium-titanyl phosphate (KTP) laser (e.g., a GreenLight™ laser) is used as a light source. In one embodiment the light source emits light at or near the absorption wavelength of the activating agent or at least one of the activating agents, if several are included in the composition.

The most intense fluorescence (e.g., emission) from a fluorochrome dye occurs when it is irradiated with wavelengths close to the peak of the absorption wavelength (i.e., excitation curve). Accordingly, in one embodiment, the actinic light is at a wavelength of about the absorption wavelength of the activating agent. In one embodiment, the actinic light has a wavelength in the range from about 470 nm to about 550 nm. In another embodiment, the actinic light has a wavelength in the range from about 470 nm to about 520 nm. In yet another embodiment, an argon laser provides actinic light in the wavelength range from about 470 nm to about 520 nm. In a further embodiment, the actinic light has a wavelength of about 530 nm to about 535 nm. In still another embodiment, the source of actinic light in the wavelength range of about 530 nm to about 535 nm is a KTP laser. In this embodiment the source is a KTP laser set at about 532 nm. In another embodiment, a photocuring device is the source of actinic light.

In one embodiment, the tooth is exposed to actinic light for less than 20 minutes, in another for less than 10 minutes, in another for less than 5 minutes. In one embodiment the tooth is exposed to actinic light for less than 4, 3, 2, or 1 minute. In one embodiment, the invention provides a method for whitening teeth at least 2 shades in about 1 minute. In some embodiments, there is no significant post-treatment sensitivity. In other embodiments, there is no post-treatment sensitivity.

In one embodiment, the tooth whitening composition is applied and the tooth is exposed to multiple applications of actinic light, for a time of about 4 to about 6 seconds each tooth per exposure. In some embodiments, the tooth is exposed to actinic light at least two, three, four, five or six times. In some embodiments, a fresh application of the tooth whitening composition is applied before each exposure to actinic light. In some embodiments, the total exposure to actinic light is less than about one minute. In other embodiments, the total exposure to actinic light is less than about 60, 40, 30, or 20 seconds.

In one embodiment, the tooth is whitened at least 7 shades, 6 shades, 5 shades, 4 shades, 3 shades, 2 shades or 1 shade. Shades can be determined before and after treatment using any of a number of shade guides, including, e.g., the VITA® (Vita Zahnfabrik H. Rauter GmbH & Co., KG), CHROMASCOP® (Ivoclar Vivadent, Inc.) or BIODENT (Dentsply International) shade guides. Optionally, a shade taking system, e.g., the ShadeEye NCC Dental Chroma Meter, can be employed to determine shade before and/or after treatment.

In one embodiment, the tooth is whitened at least two shades, three shades, four shades, five shades, six shades or seven shades in less than about one minute of total exposure time to actinic light. In some embodiments, the tooth is whitened at least two shades, three shades, four shades, five shades, six shades or seven shades in less than about 40 seconds of total exposure time to actinic light. In some embodiments, the tooth is whitened at least two shades, three shades, four shades, five shades, six shades or seven shades in less than about 30 seconds of total exposure time to actinic light. In some embodiments, the tooth is whitened at least two shades, three shades, four shades, five shades, six shades or seven shades in less than about 20 seconds or even less than about 10 seconds of total exposure time to actinic light.

In one embodiment, the risk of transient inflammation of the pulp by percolation of hydrogen peroxide is reduced, not significant and/or eliminated. Without wishing to be bound by any particular theory, inflammation of the pulp is thought to be caused by percolation of hydrogen peroxide into the pulp tissue. In some embodiments, the synergistic effect of the activating agents (e.g., Eosin B and Erythrosin B), and the actinic light results in an instantaneous and complete photochemical reaction. Accordingly, exposure of the tooth, the pulp, and/or the surrounding tissues to the oxidizing agent and/or other components in the composition is dramatically reduced.

In yet another aspect, the invention provides a method for tooth whitening comprising application of actinic light and a composition of the invention (any of the compositions described herein) to at least one tooth such that the tooth is whitened at least about two shades in less than about 10 minutes. In another embodiment, the tooth is whitened at least about two shades in less than about 5 minutes, less than about 4 minutes, less than about 3 minutes, less than about 2 minutes or in about 1 minute. In some embodiments, the teeth are whitened at least about 3 shades, 4 shade or 5 shades. In some embodiments, there is no significant post-treatment sensitivity or no post-treatment sensitivity.

In yet another aspect, the invention provides a kit for preparing or applying a tooth whitening composition in accordance with the present invention. In one embodiment, the kit includes an oxidizing agent and an activating agent that has an emission wavelength between about 400 nm and about 570 nm. The composition can be any of the compositions of the present invention. In one embodiment, the composition is not combined, and may optionally include apparatus to combine two or more components or premixes of the composition. In another embodiment the composition does not require any combination (i.e., it is ready to use and does not require any pre-mixing chair-side).

In another embodiment, the kit includes a composition of the invention and directions for application. Additionally or alternatively, the kit can include apparatus for application (e.g., brushes or trays or both). The kit can also include charts or other information helpful in assessing the whitening effect desired and/or achieved by the methods and compositions of the invention. The kit can also include a source of actinic light.

Identification of equivalent compositions, methods and kits are well within the skill of the ordinary practitioner and would require no more than routine experimentation, in light of the teachings of the present disclosure. Practice of the invention will be still more fully understood from the following examples, which are presented herein for illustration only and should not be construed as limiting the invention in any way.

Example 1

Preparation of an Exemplary Whitening Composition and Activation by Actinic Light A premix was prepared by mixing 4 mg of Eosin B, 1 mg Erythrosine B, 450 mg fumed silica, and 45 mg sodium perborate. Separately, the pH of a 50% hydrogen peroxide solution was adjusted to pH 6 using sodium acetate solution. Approximately 4-6 ml of the adjusted hydrogen peroxide solution was then added to the premix in a plastic mixing chamber and immediately applied.

The gel was applied to frontal surface of the teeth of each subject beginning from the frontal anterior incisors, followed by the posteriors, and finally the posterior incisors. The gel was activated by a KTP laser set at a continuous wave of 0.5 watts. The laser was applied to each tooth for 2-3 seconds. During this time, the gel turned from orange-red to transparent and eventually became dull. After 3-4 minutes for two full arches from premolar to premolar, the gel was aspirated, and the teeth were lightly scrubbed with a cotton roll to clean the surface of the enamel. A second coating of gel was applied using fresh gel and activated with the KTP laser as described above. Up to six consecutive applications were performed to achieve the desired whitening effect for each patient. The duration of the sessions typically did not exceed 40 minutes.

Comparative Example 2

Whitening Effect of Composition

A comparative study was conducted on 10 volunteers between an exemplary composition of the present invention and the SMARTBLEACH laser teeth whitening systems, which is a composition comprising Rhodamine B and hydrogen peroxide. The shade of each patient's teeth was recorded prior to application of whitening composition.

Teeth were coated with the composition prepared in Example 1 and exposed to actinic light from a green laser set at 532 nm for one minute for the entire mouth (4-5 seconds per tooth) and then the composition was removed. The comparative composition was applied to the teeth and exposed to light from a green laser set at 532 nm for 30 seconds per tooth and then left on the surface of the tooth for 10 minutes, in accordance with the manufacturer instructions provided with the composition. The comparative composition required at least 3 to 4 applications, for a total duration of about 1.5 hours for the entire mouth. The composition was removed from each volunteer and the teeth were irrigated with water. The teeth were then evaluated using the VITA scale for the whitening effect of the compositions. Patients were also evaluated for any post-treatment sensitivity by asking them to rate the level of pain experience if any.

The Smartbleach™ treatment resulted in a shade change of one to two shades in the yellow group, while the exemplary composition of the present invention resulted in a shade change of 5 shades in the yellow group, e.g., $A_4$ to $B_1$ VITA scale. In the "yellow group" ($A_4$-$A_1$), treatment with the exemplary composition of the present invention resulted in shade changes of 4-5 shades, resulting in shades in the "white group" ($B_1$-$B_2$). Treatment with the exemplary composition for teeth in the "grey" ($C_4$-$C_1$) and "grey-brown" ($D_4$-$D_2$) groups showed changes of 2-3 shades in the first session.

The following evaluation scale of post-sensitivity was used:

| | |
|---|---|
| Level 0 | No sensitivity to thermal stimuli or any kind of pain following treatment. |
| Level 1 | Sensitivity to thermal stimuli that lasts for a few seconds. |
| Level 2 | Pain or discomfort that occurs due to thermal stimuli and lasts for more than one minute. Optional pain treatment with analgesics. |
| Level 3 | Pain or discomfort that occurs automatically, requiring use of analgesics to control the pain. |

Following treatment with the Smartbleach™ system, all ten subjects experienced pain from Level 1 to Level 3. Following treatment with the exemplary composition of the present invention, nine subjects experienced no pain (e.g., Level 0), and only one subject experienced pain of Level 1.

Comparative Example 3

Effect of Actinic Light Source

A study was conducted on 28 volunteers comparing the effect of different actinic light sources in whitening with the composition of Example 1. A prophylactic session was performed on each patient 3-4 days before the bleaching session. The shade of each patient's teeth was recorded prior to application of whitening composition.

Teeth were coated with the composition prepared in Example 1 and exposed to different sources of actinic light: a green laser (KTP) at 532 nm, a blue (argon) laser at 480-414 nm, a photocuring halogen lamp, and a LED photocuring device.

The activation was performed in the different patients for the left or the right sides of their dental arches according to an activation randomization mode. Specifically, a first patient's right side was activated with the 532 nm green laser, while the left side was activated with the 480 nm-514 nm blue-green laser. A second patient's right side was activated with the photocuring halogen lamp, while the left side was activated with the LED photocuring device. A third patient's right side was activated with the 532 nm green laser, while the left side was activated with the photocuring halogen lamp. A fourth patient's right side was activated with the 532 nm green laser, while the left side was activated with the LED photocuring device. A fifth patient's right side was activated with the 480 nm-514 nm blue-green laser, while the left side was activated with the photocuring halogen lamp. A sixth patient's right side was activated with the 480 nm-514 nm blue-green laser, while the left side was activated with the LED photocuring device.

The composition was removed from the teeth of each volunteer and the teeth were irrigated with water. The teeth were then evaluated using the VITA scale for the whitening effect of the compositions.

Activation by different photocuring devices produced comparable results. The speed of activation with the green laser and the blue-green laser was 4-5 seconds per tooth, while the speed of activation with the photocuring devices was about 10 seconds per tooth. Accordingly, a whitening session employing the green laser or the blue-green laser for the entire mouth would typically take approximately 30 minutes, and a session with a photocuring device would typically take approximately 40 minutes.

What is claimed:

1. A tooth whitening composition for whitening a tooth in vivo in the gingiva of a patient comprising:
   an oxidizing agent selected from peroxide, peroxy acid, hydrogen peroxide, carbamide peroxide, and alkali metal percarbonates;
   an activating agent consisting of an amount effective to activate said oxidizing agent that is up to 12% Eosin B; and
   sodium perborate.

2. The composition according to claim 1, wherein the composition comprises a thickening agent.

3. The composition according to claim 2, wherein the thickening agent is silicon dioxide and/or fumed silica having a particle size less than one micron.

4. The composition according to claim 1, wherein the composition comprises a hydrophilic gelling agent.

5. The composition according to claim 1, wherein the pH of the composition is between about 4 and about 10.

6. A kit for tooth whitening comprising:
   a composition according to claim 1; and
   an apparatus for applying the composition.

7. A kit for tooth whitening comprising:
   a composition according to claim 1; and
   instructions for determining a composition application time to achieve a whitening effect.

8. The composition according to claim 1, wherein said activating agent consists of from about 0.06% to 1.2% Eosin B.

9. The composition according to claim 1, which further comprises an activating agent consisting of from about 0.005% to about 0.15% Erythrosin.

* * * * *